(12) United States Patent
Koehler et al.

(10) Patent No.: US 8,385,621 B2
(45) Date of Patent: Feb. 26, 2013

(54) METHOD FOR RECONSTRUCTION IMAGES AND RECONSTRUCTION SYSTEM FOR RECONSTRUCTING IMAGES

(75) Inventors: Thomas Koehler, Norderstedt (DE); Peter Forthmann, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 918 days.

(21) Appl. No.: 12/296,116

(22) PCT Filed: Mar. 15, 2007

(86) PCT No.: PCT/IB2007/050896
§ 371 (c)(1),
(2), (4) Date: Oct. 6, 2008

(87) PCT Pub. No.: WO2007/113704
PCT Pub. Date: Oct. 11, 2007

(65) Prior Publication Data
US 2009/0116717 A1 May 7, 2009

(30) Foreign Application Priority Data
Apr. 6, 2006 (EP) .................................. 06112281

(51) Int. Cl.
*G06K 9/20* (2006.01)
*G06T 1/00* (2006.01)
(52) U.S. Cl. ........................................ 382/131; 378/901
(58) Field of Classification Search .................. 382/128, 382/130–132, 184, 276, 284–287, 291, 293, 382/294; 378/4–20, 91, 98, 98.8, 98.12, 378/114–116, 210, 901
See application file for complete search history.

(56) References Cited

U.S. PATENT DOCUMENTS

| | | | |
|---|---|---|---|
| 5,208,746 A | 5/1993 | King et al. | |
| 5,513,236 A | 4/1996 | Hui | |
| 6,014,419 A * | 1/2000 | Hu | 378/4 |
| 6,381,298 B2 * | 4/2002 | Proksa et al. | 378/15 |
| 6,665,370 B2 | 12/2003 | Bruder et al. | |
| 7,010,149 B1 * | 3/2006 | Knoplioch et al. | 382/128 |
| 2004/0101086 A1 * | 5/2004 | Sabol et al. | 378/4 |

(Continued)

FOREIGN PATENT DOCUMENTS

| | | |
|---|---|---|
| GB | 2361613 A | 10/2001 |
| WO | 9942949 A1 | 8/1999 |

(Continued)

OTHER PUBLICATIONS

Gregor, J., et al.; Conebeam X-Ray Computed Tomography with an Offset Detector Array; 2003; IEEE; pp. II-803-806.

(Continued)

*Primary Examiner* — Anastasia Midkiff

(57) ABSTRACT

A reconstruction method for an image of an object, the reconstruction method comprising receiving a first projection data set representing information about said object, receiving a second projection data set representing information about said object, reconstructing a first image of said object using the first projection data set, reconstructing a second image of said object using the second projection data set, performing a registration between the first image and the second image, and fusing the first image and the second image to said image of said object, wherein the first projecting data set and the second projecting data set are achieved by using a single radiation type.

19 Claims, 3 Drawing Sheets

| U.S. PATENT DOCUMENTS | | | |
|---|---|---|---|
| 2004/0240604 A1 | 12/2004 | Wang et al. | |
| 2005/0084060 A1 | 4/2005 | Seppi et al. | |
| 2005/0105828 A1 | 5/2005 | Oosawa | |
| 2005/0111757 A1 | 5/2005 | Brackett et al. | |
| 2007/0253528 A1* | 11/2007 | Ning et al. | 378/15 |
| 2008/0265166 A1* | 10/2008 | Shekhar et al. | 250/363.03 |

FOREIGN PATENT DOCUMENTS

| WO | 0180184 A1 | 10/2001 |
|---|---|---|

OTHER PUBLICATIONS

Hsieh, H.; Computed Tomography; 2003; SPIE Press, Belliingham; Chapter 3.8; pp. 87-90.

Rohr: "Elastic Registration of Multimodal Medical Images: A Survey"; Kunstliche Intelligenz, Heft Mar. 2000, Arendtap Verlag, Bremen, pp. 11-17.

* cited by examiner

METHOD FOR RECONSTRUCTION IMAGES AND RECONSTRUCTION SYSTEM FOR RECONSTRUCTING IMAGES

The invention relates to a method for reconstruction images, a reconstruction system for reconstructing images, a tomography apparatus, a computer readable medium and a program element, in particular to a method for reconstruction of a computed tomography image.

Computed tomography (CT) is a process of using digital processing to generate a three-dimensional image of the internal of an object under investigation (object of interest, object under examination) from a series of two-dimensional x-ray images taken around a single axis of rotation. The reconstruction of CT images can be done by applying appropriate algorithms.

A basic principle of CT imaging is that projection data of an object under examination are taken by detectors of a CT system. The projection data represent information of the object passed by radiation beams. To generate an image out of the projection data these projection data (line integrals) can be back-projected leading to a two-dimensional image, i.e. representing a disc. Out of a plurality of such two-dimensional images a so called voxel representation, i.e. a representation of three dimensional pixels, can be reconstructed. In case that the detectors are already arranged in form of a plane, two-dimensional projection data are achieved and the result of the back-projection is a three-dimensional voxel. That is, in modern, more sophisticated so called "cone-beam" CT and reconstruction methods the projection data of two-dimensional detectors, i.e. detectors having a plurality of detecting elements arranged in form of a matrix, are directly back-projected into a three-dimensional distribution of voxels in one single reconstruction step. The current trend in computed tomography goes into the direction of increasing the number of detector rows and thus toward a very large coverage of the object under examination.

It is believed that so-called axial cone-beam CT will become the most attractive acquisition protocol for future CT systems as the detectors become large enough to cover the entire region of interest in a single rotation. Unfortunately, the reconstruction of the axial cone-beam data suffers from the so-called missing data problem. A circular trajectory of a scanning unit, i.e. a radiation source and the associated detector, does not provide sufficient data to allow a stable and artifact free reconstruction. One possibility to reduce the artifacts is to apply a second-pass correction step, which is, for example, described in J. Hsieh, "Computed Tomography", SPIE press, Bellingham, 2003, Chapter 3.8. Here, strong gradients in the initial reconstruction are extracted and artifacts caused by these gradients by the reconstruction algorithm can be predicted and thus eliminated in the image. One shortcoming of this method is, that it handles axially truncated projections very badly. During a circular scan, parts of the object are irradiated, which cannot be reconstructed, since these parts have less than 180 degree of illumination, i.e. forming a region with less than 180 degree of illumination. Any strong gradient in this region can cause severe artifacts also in regions that can be reconstructed. Since these structures, which cause the strong gradients, are not recovered by the initial reconstruction, the corresponding artifacts cannot be removed by the second-pass technique. As a consequence, the second pass artifact correction method can be applied only to a rather small portion of the field of view.

It may be desirable to provide an alternative reconstruction method for an image, a reconstruction system for reconstructing images, a tomography apparatus, a computer readable medium and a program element which may be less prone to artifacts in the reconstructed image and may have a greater coverage of the field of view.

This need may be met by a reconstruction method for an image, a reconstruction system for reconstructing images, a tomography apparatus, a computer readable medium and a program element according to the independent claims.

According to an exemplary embodiment of a reconstruction method for an image of an object under examination, the reconstruction method comprising: receiving a first projection data set representing information about said object under examination, receiving a second projection data set representing information about said object under examination, reconstructing a first image of said object under examination using the first projection data set, reconstructing a second image of said object under examination using the second projection data set, performing a registration between the first image and the second image, and fusing the first image and the second image to said image of said object under examination, wherein the first projecting data set and the second projecting data set are achieved by using a single radiation type.

According to an exemplary embodiment a computer readable medium is provided in which a program for producing an image based on projection data of a tomography system is stored, which program, when executed by a processor, is adapted to control a method comprising: receiving a first projection data set representing information about said object under examination, receiving a second projection data set representing information about said object under examination, reconstructing a first image of said object under examination using the first projection data set, reconstructing a second image of said object under examination using the second projection data set, performing a registration between the first image and the second image, and fusing the first image and the second image to said image of said object under examination, wherein the first projection data set and the second projecting data set are achieved by using a single radiation type.

According to an exemplary embodiment a program element for producing an image based on projection data of a tomography system is provided, which program, when executed by a processor, is adapted to control a method comprising: receiving a first projection data set representing information about said object under examination, receiving a second projection data set representing information about said object under examination, reconstructing a first image of said object under examination using the first projection data set, reconstructing a second image of said object under examination using the second projection data set, performing a registration between the first image and the second image, and fusing the first image and the second image to said image of said object under examination, wherein the first projecting data set and the second projecting data set are achieved by using a single radiation type.

According to an exemplary embodiment a reconstruction system for reconstructing an image of an object under examination comprises a receiving unit adapted to receive a first projection data set representing information about said object under examination and a second projection data set representing information about said object under examination a reconstructing unit adapted to reconstruct a first image of said object under examination using the first projection data set and a second image of said object under examination using the second projection data set, wherein the first projecting data set and the second projecting data set are achieved by using a single radiation type. Further, the reconstruction system comprises a registration unit adapted to perform a registration between the first image and the second image, and a fusing unit adapted to fuse the first image and the second image to said image of said object under examination.

According to an exemplary embodiment a tomography apparatus comprises a radiation source, a radiation detector, and a reconstruction system according to an exemplary embodiment of the invention, wherein the radiation detector is adapted to detect and transmit the first projection data set and the second projection data set.

It may be seen as the gist of an exemplary embodiment of the present invention that a reconstruction method for an image of an object under examination is provided, wherein the method comprises the independent reconstruction of two images out of two different projection data sets, which data sets where achieved by using the same radiation type, e.g. using an x-ray radiation source. Even the same radiation source can be used in generating the two projection data sets. These two images are then fused after an image registration between these two images is performed. Due to this image registration it might be possible to compensate for motion of the object under examination between the time when the first projection data set is recorded and the time when the second projection data set is recorded. Thus, the reconstruction method may be less sensitive to movements of the object under examination between two scans, e.g. the movement of a patient. The fusing of the two images, after the image registration is performed, to one final image may facilitate that a greater field of view is corrigible, in particular it may be possible that the entire region that was irradiated while taking the projection data sets may be corrigible.

Image registration, which is also called image matching, is well known to the person skilled in the art and refers to the task to compute spatial transformations, which map each point of an image onto its (physically) corresponding point of another image. More information about this methods can be gathered from the review article "Elastic Registration of Multimodial Medical Images: A Survey", K. Rohr, Künstliche Intelligenz, Heft 3/00, arenDTaP Verlag, Bremen, pg. 11 to 17 and the references cited therein, which are hereby incorporated herein in whole by reference.

This reconstruction method may be usable in the field of tomography apparatuses, e.g. a computed tomography apparatus, in particular in an X-ray computer tomography.

In the following, further exemplary embodiments of the reconstruction method will be described. However, these embodiments apply also for the reconstruction system for reconstructing images, the tomography apparatus, the computer readable medium and the program element.

According to another exemplary embodiment one of the first projection data set and the second projection data set is recorded by using a non-planar scanning path, and the other one of the projection data sets is recorded by using a planar scanning path.

According to another exemplary embodiment of the reconstruction method the first data set is a data set recorded in a helical scan of said object under examination. Preferably, the helical scan is a so-called low-dose helical scan, i.e. a scan in which only a low dose of radiation is emitted. Such a helical scan may represent a non-planar scanning path.

In particular by using a low-dose helical scanning it may be possible to acquire additional data which can be used to improve the quality of the final image, when the first image is fused with the second image, while the increase of a dose of radiation which penetrates the object under examination may not be substantially increased. It should be noted that of course the first projection data set does not have to be the first one which is taken, i.e. the first data set can be recorded after the second data set was recorded.

According to another exemplary embodiment of the reconstruction method the second data set is a data set recorded in a circular cone-beam scan of said object under examination. Such a helical scan may represent a planar scanning path.

In particular, the combination of a low-dose helical scan and a circular cone-beam scan, or at least an approximately circular cone-beam scan, may be advantageous since after the registration the two independent images may be fused into one final image that may cover the entire region that was irradiated by the circular scan. Further, the combination of these two different scans may be a possibility to overcome the problems of the prior art in providing sufficient data to allow a stable and artifact free reconstruction. That is, it may be a possibility to overcome the so-called missing data problem of axial cone-beam data. In particular, according to an exemplary embodiment the first projection data set is recorded using a different projection method than that used for the recording of the second projection data set.

According to another exemplary embodiment of the reconstruction method the registration is one of the group consisting of rigid registration and non-rigid registration. A non-rigid registration may be a affine transformation or an elastic registration (elastic transformation), e.g. a landmark-based elastic registration, or intensity-based elastic registration.

According to another exemplary embodiment of the reconstruction method the landmark-based elastic registration is one of the group consisting of: curves-landmark based elastic registration, surfaces-landmark based elastic registration, volume-landmark based elastic registration and point-landmark based elastic registration. In particular, a point-landmark based elastic registration using thin plate splines including isotropic or anisotropic errors may be used.

The above-mentioned different registrations (transformations) may be well suited to compute spatial transformations, which map each point of an image onto its (physically) corresponding point of another image, i.e. may be well suited to prepare the two images in such a way that they can be fused to one final image.

According to another exemplary embodiment the reconstruction method further comprising performing a second pass correction on the fused image.

Such a second pass correction may be advantageous to remove artifacts in the entire fused or final image obtained by the reconstruction method. An example of a second pass correction method is described in J. Hsieh, "Computed tomography", SPIE press, Bellingham, 2003, Chapter 3.8, which is hereby incorporated herein by reference. Summarizing, by a second pass correction the projection data set is: 1. back-projected to get an intermediate image. 2. Strong gradients, i.e. areas with high contrast, are determined. 3. Afterwards the influence of these strong gradients, i.e. portions of the object under examination in which a great difference in absorption is present, onto the projection are calculated. 4. These influences or errors are then substracted from the original projection, which are 5. back-projected to achieve a final image which exhibits less artifacts than the intermediate image.

According to another exemplary embodiment the reconstruction method further comprising performing a 2D-3D registration. That is, a transformation which describe projections of three-dimensional (3D) images onto two-dimensional (2D) images.

The examination of the object of interest, e.g. the analysis and reconstruction of cardiac or lung computed tomography data taken by a scanning unit and/or a tomography apparatus according to the invention as well as the reconstruction system, may be realized by a computer program, i.e. by software, or by using one or more special electronic optimization circuits, i.e. in hardware, or in hybrid form, i.e. by software components and hardware components. The computer program may be written in any suitable programming language, such as, for example, C++ and may be stored on a computer-readable medium, such as a CD-ROM. Also, the computer program may be available from a network, such as the WorldWideWeb, from which it may be downloaded into image processing units or processors, or any suitable computers.

It should be noted in this context, that the present invention is not limited to computed tomography, but may include the use of C-arm based 3D rotational X-ray imaging, magnetic resonance imaging, positron emission tomography or the like. It should also be noted that this technique may in particular be useful for medical imaging like diagnosis of the heart or lungs of a patient.

It may be seen as the gist of an exemplary embodiment of the present invention that missing data of a (substantially) circular cone-beam scan may be derived from an initial low-dose helical scan. From the two projection data sets (helical scan and circular cone-beam scan) two images are independently reconstructed. Afterwards an elastic registration of the two images may be performed in order to compensate for patient motion between the two scans. After the registration the two images can be fused into one image that may cover the entire region that was irradiated by the circular scan. A second pass correction method may finally be applied to remove artifacts in the entire image obtained by the circular scan. To improve the quality of the registration in particular for a region where object points are illuminated over less than 180 degrees, 2D-3D registration techniques may be used additionally.

These and other aspects of the present invention will become apparent from and elucidated with reference to the embodiment described hereinafter.

An exemplary embodiment of the present invention will be described in the following, with reference to the following drawings.

The illustration in the drawings is schematically. In different drawings, similar or identical elements are provided with the similar or identical reference signs.

FIG. 1 shows an exemplary embodiment of a computed tomography scanner system which projection data may be handled by a reconstruction method according an embodiment of the invention.

Figure 1:
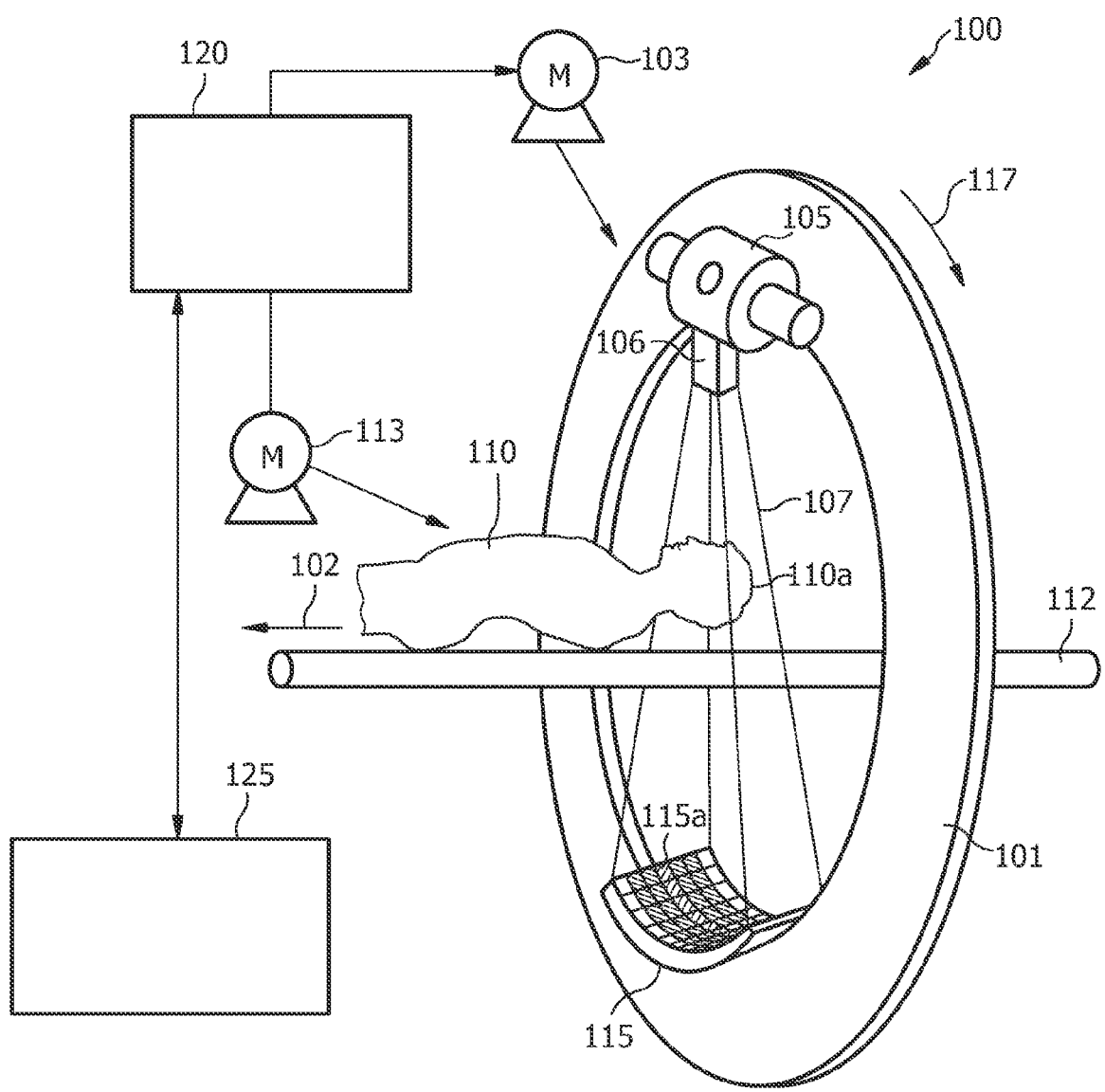
FIG. 1 shows a simplified schematic representation of a computed tomography system.

The computed tomography apparatus 100 depicted in FIG. 1 is a cone-beam CT scanner. The CT scanner depicted in FIG. 1 comprises a gantry 101, which is rotatable around a rotational axis 102. The gantry 101 is driven by means of a motor 103. Reference numeral 105 designates a source of radiation such as an X-ray source, which emits polychromatic or monochromatic radiation.

Reference numeral 106 designates an aperture system which forms the radiation beam emitted from the radiation source unit to a cone-shaped radiation beam 107. The cone-beam 107 is directed such that it penetrates an object of interest 110 arranged in the center of the gantry 101, i.e. in an examination region of the CT scanner, and impinges onto the detector 115 (detection unit). As may be taken from FIG. 1, the detector 115 is arranged on the gantry 101 opposite to the radiation source unit 105, such that the surface of the detector 115 is covered by the cone beam 107. The detector 115 depicted in FIG. 1 comprises a plurality of detection elements 115a each capable of detecting X-rays which have been scattered by, attenuated by or passed through the object of interest 110. The detector 115 schematically shown in FIG. 1 is a two-dimensional detector, i.e. the individual detector elements are arranged in a plane, such detectors are used in so called cone-beam tomography.

During scanning the object of interest 110, the radiation source unit 105, the aperture system 106 and the detector 115 are rotated along the gantry 101 in the direction indicated by an arrow 117. For rotation of the gantry 101 with the radiation source unit 105, the aperture system 106 and the detector 115, the motor 103 is connected to a motor control unit 120, which is connected to a control unit 125 (which might also be denoted and used as a calculation, reconstruction or determination unit). The control unit 125 can be formed by a processor which can be adapted to perform a reconstruction method according to an exemplary embodiment of the invention and which can form a reconstruction system according to an exemplary embodiment of the present invention.

In FIG. 1, the object of interest 110 is a human being which is disposed on an operation table 112. During the scan of a head 110a, a heart, a lung or any other part of the human being 110, while the gantry 101 rotates around the human being 110, the operation table 112 may displace the human being 110 along a direction parallel to the rotational axis 102 of the gantry 101. This may be done using a motor 113. By this, the heart is scanned along a helical scan path. The operation table 112 may also be stopped during the scans to thereby measure signal slices. This helical scanning is done with a low-dose radiation of the radiation source and is used to achieve a first data set of data representing information about the heart.

After this low-dose helical scan a cone-beam scan having a substantially circular trajectory, i.e. a circular scan, is performed to achieve a second data set representing the object under examination, e.g. the heart of a patient. During the circular scan is performed there is no displacement in a direction parallel to the rotational axis 102, but only the rotation of the gantry 101 around the rotational axis 102. Of course the sequence of the helical scan and the circular trajectory scan can be changed so that firstly the circular trajectory scan is performed.

Optionally, an electrocardiogram device can be provided which measures an electrocardiogram of the heart of the human being 110 while X-rays attenuated by passing the heart are detected by detector 115. The data related to the measured electrocardiogram are transmitted to the control unit 125.

The detector 115 is connected to the control unit 125. The control unit 125 receives the detection result, i.e. the read-outs from the detection elements 115a of the detector 115 and determines a scanning result on the basis of these read-outs. Furthermore, the control unit 125 communicates with the motor control unit 120 in order to coordinate the movement of the gantry 101 with motors 103 and 113 with the operation table 112.

The control unit 125 may be adapted for reconstructing an image from read-outs of the detector 115. A reconstructed image generated by the control unit 125 may be output to a display (not shown in FIG. 1) via an interface.

The control unit 125 may be realized by a data processor to process read-outs from the detector elements 115a of the detector 115.

The computed tomography apparatus shown in FIG. 1 may capture multi-cycle cardiac computed tomography data of the heart. In other words, when the gantry 101 rotates and when the operation table 112 is shifted linearly, then a helical scan is performed by the X-ray source 105 and the detector 115 with respect to the heart. During this helical scan, the heart may beat a plurality of times and multiple RR-cycles are covered. During these beats, a plurality of cardiac computed tomography data are acquired. Simultaneously, an electrocardiogram may be measured by the electrocardiogram unit. After having acquired these data, the data are transferred to the control unit 125, and the measured data may be analyzed retrospectively.

Figure 2:
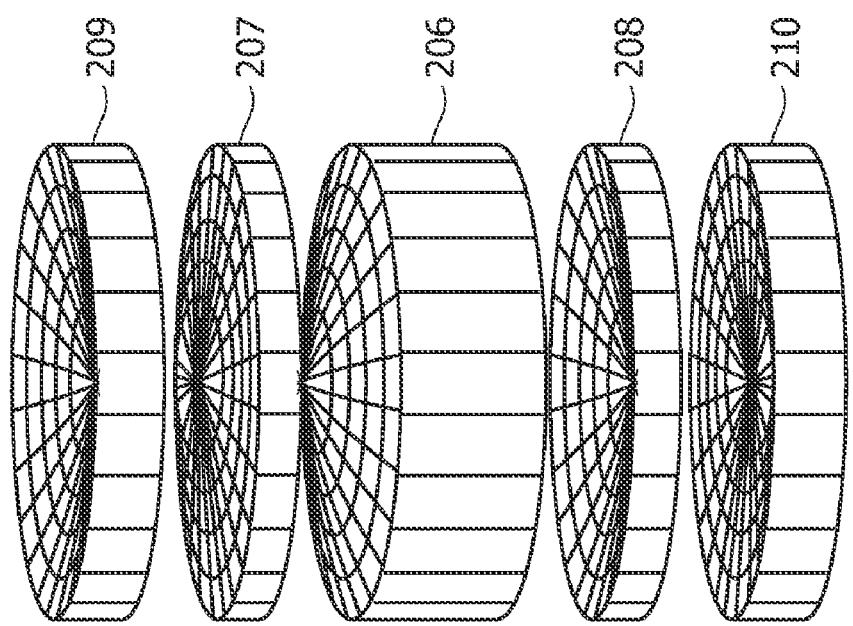
FIG. 2 shows a schematic drawing of an acquisition geometry for cone-beam CT.
Figure 2:
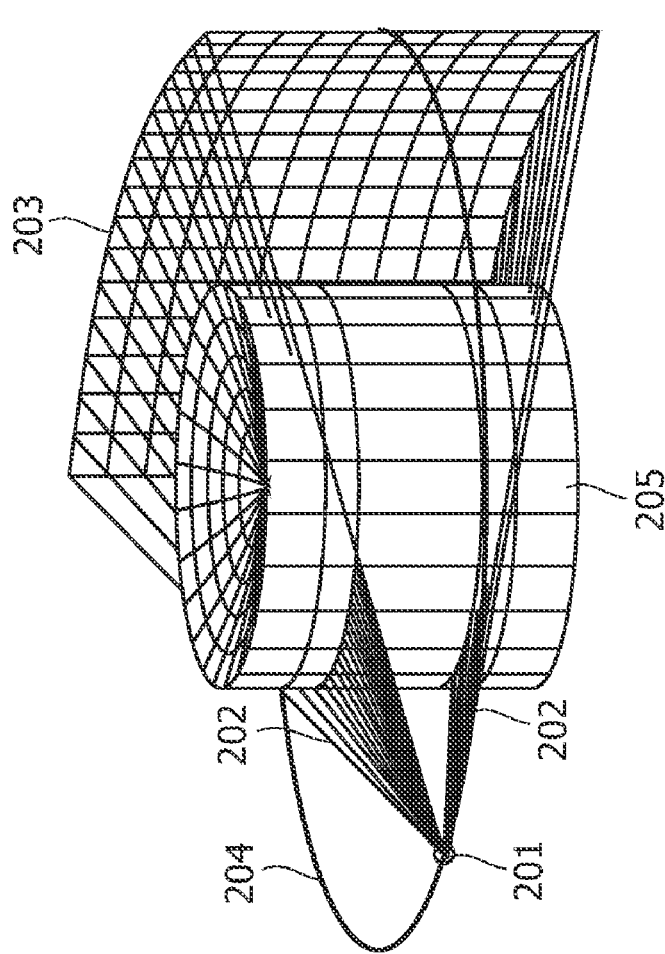

FIG. 2 shows a schematic drawing of an acquisition geometry for cone-beam CT. In particular FIG. 2 illustrates the so-called missing data problem of a circular cone-beam scan.

In the left part of FIG. 2 the acquisition geometry for a cone-beam CT is shown. A radiation source 201 is schematically shown as a black dot. The radiation source emits radiation beams, which are schematically shown in FIG. 2 as the lines 202 and which run in the form of a cone from the radiation source 201 to a radiation detector 203. Both, the radiation source 201 as well as the radiation detector 203 run on a circular path around an object under examination. The circular path is schematically shown in FIG. 2 as the circle 204. As the scanning unit, i.e. the radiation source 201 and the associated radiation detector 203, running on the circular path a volume 205 is irradiated. This volume 205 comprises five parts, which are shown in more detail on the right side of FIG. 2. A center part 206 is irradiated (illuminated) over the whole circle, i.e. represents object points with 360 degrees of illumination. The adjacent middle parts 207 and 208 are irradiated over at least 180 degrees of the circularly path 204, i.e. represent object points with at least 180 degrees of illumination. While the outer parts 209 and 210 are irradiated over less then 180 degrees, i.e. represents object points with less than 180 degrees illumination. A reconstruction is only possible for object points with at least 180 degrees illumination. Thus, the object points of the outer parts 209 and 210 can not be reconstructed. But also for the object points of the middle parts 207 and 208 data are missing, i.e. the redundancy of the data is lower in these middle parts than in the center part 206, which may lead to an increase of artifacts in the reconstruction.

Figure 3:
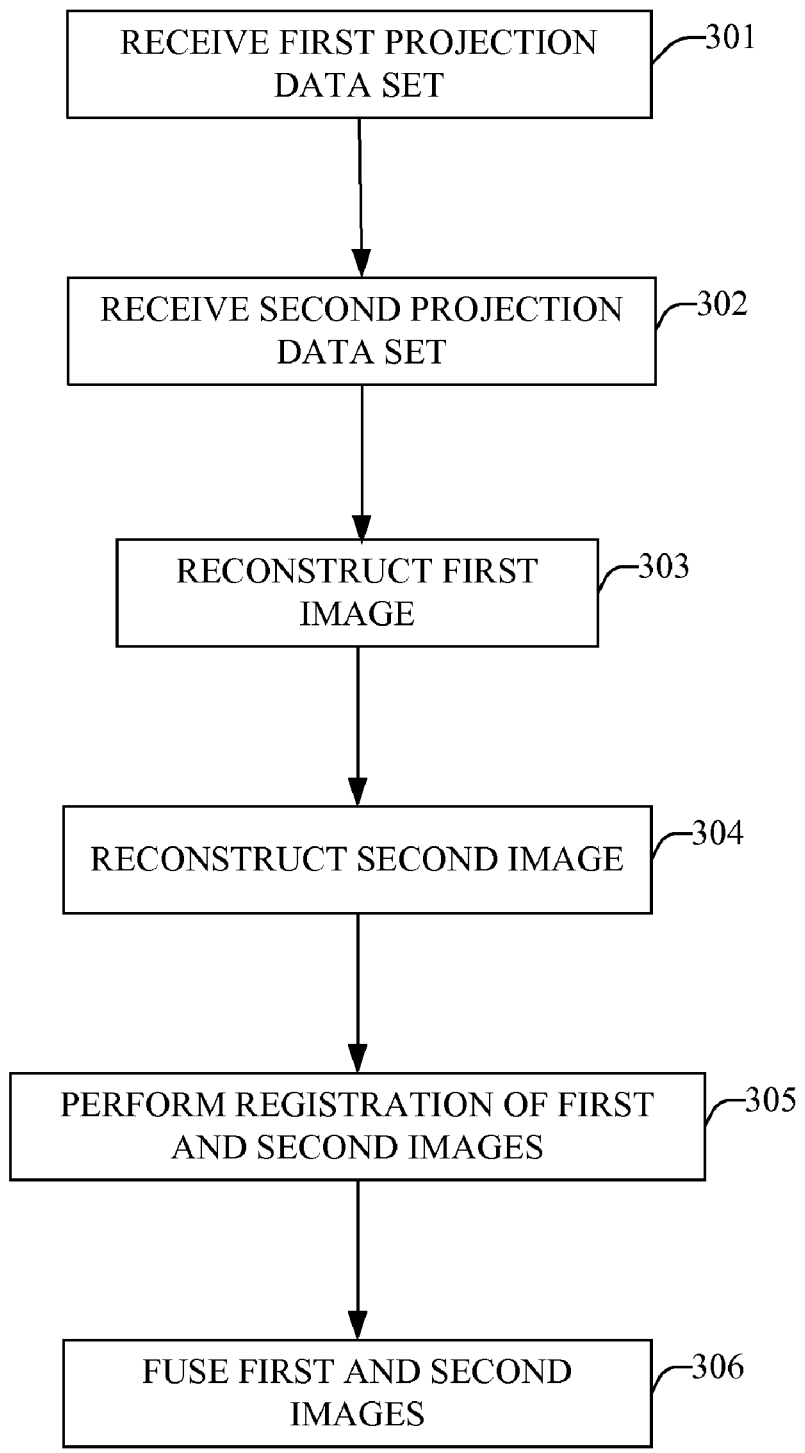
FIG. 3 shows a schematic flow chart of a reconstruction method according to an exemplary embodiment of the invention.

In the following the reconstruction method according to an exemplary embodiment of the invention will be described in more detail with reference to the schematic flow chart of FIG. 3.

In a first step 301 a first projection data set, e.g. from a low-dose helical scan, is received by a reconstruction unit. In a second step 302 a second projection data set, e.g. from a substantially circular cone-beam scan, is received by the reconstruction unit. Thereafter, the reconstruction unit reconstructs a first image out of the first projection data set 303 and a second image out of the second projection data set 304. The two images are reconstructed independently from each other. In a next step a registration of the two images is performed 305. Preferably, an elastic registration is performed. At least in the areas which have less than 180 degrees of illumination an additional 2D-3D registration is performed. After the registration the two images are fused to one image 306 which covers the entire region that was irradiated by the circular scan. Afterwards an optional second pass correction can be performed to remove artifacts in the entire image.

By using this reconstruction method, i.e. a method in which a first image reconstructed out of projection data of a low-dose helical scan and a second image reconstructed out of projection data of a circular cone-beam scan are combined, a final image may be achieveable which is less prone to artifacts and may have a greater coverage of the field of view It should be noted that the term "comprising" does not exclude other elements or steps and the "a" or "an" does not exclude a plurality. Also elements described in association with different embodiments may be combined. It should also be noted that reference signs in the claims shall not be construed as limiting the scope of the claims.

The invention claimed is:

1. A reconstruction method for an image of an object under examination, the reconstruction method comprising:
receiving a first projection data set representing information about said object under examination;
receiving a second different projection data set representing information about said object under examination;
reconstructing a first image of said object under examination using the first projection data set;
reconstructing a second image of said object under examination using the second projection data set;
performing a registration between the first image and the second image;
performing an additional 2D-3D registration for areas of the first and second images that have less than 180 degrees of illumination; and
fusing the first image and the second image to produce said image of said object under examination, wherein the first projecting data set and the second projecting data set are achieved by using a single radiation type.

2. The reconstruction method according claim 1, wherein one of the first projection data set and the second projection data set is recorded by using a non-planar scanning path, and the other one of the projection data sets is recorded by using a planar scanning path.

3. The reconstruction method according to claim 1, wherein the first data set is a data set recorded in a helical scan of said object under examination.

4. The reconstruction method according to claim 1, wherein the second data set is a data set recorded in a circular cone-beam scan of said object under examination.

5. The reconstruction method according to claim 1, wherein the registration is one of the group consisting of: rigid registration; and non-rigid registration.

6. The reconstruction method according to claim 5, wherein the non-rigid registration is one of the group consisting of:
landmark-based elastic registration; and
intensity-based elastic registration.

7. The reconstruction method according claim 6, wherein the landmark-based elastic registration is one of the group consisting of: point-landmark based elastic registration; curves-landmark based elastic registration; surfaces-landmark based elastic registration; and volume-landmark based elastic registration.

8. The reconstruction method according to claim 1, further comprising: performing a second pass correction on the fused image to remove artifacts from the fused image.

9. A computer readable medium in which a program for producing an image based on projection data of a tomography system is stored, which program, when executed by a processor, is adapted to control a method comprising:
receiving a first projection data set representing information about said object under examination;
receiving a second different projection data set representing information about said object under examination;
reconstructing a first image of said object under examination using the first projection data set;

reconstructing a second image of said object under examination using the second projection data set;

performing a registration between the first image and the second image;

performing an additional 2D-3D registration for areas of the first and second images that have less than 180 degrees of illumination; and fusing the first image and the second image to produce said image of said object under examination, wherein the first projecting data set and the second projecting data set are achieved by using a single radiation type.

10. A reconstruction system for reconstructing an image of an object under examination, the reconstruction system comprising:

a receiving unit adapted to receive a first projection data set representing information about said object under examination and a second projection data set representing information about said object under examination;

a reconstructing unit adapted to reconstruct a first image of said object under examination using the first projection data set and a second image of said object under examination using the second projection data set, wherein the first projecting data set and the second projecting data set are achieved by using a single radiation type;

a registration unit adapted to perform a registration between the first image and the second image;

performing an additional 2D-3D registration for areas of the first and second images that have less than 180 degrees of illumination; and a fusing unit adapted to fuse the first image and the second image to produce said image of said object under examination.

11. A tomography apparatus comprising:
a radiation source;
a radiation detector; and
a reconstruction system according claim 10; wherein the radiation detector is adapted to detect and transmit the first projection data set and the second projection data set.

12. The tomography apparatus according o claim 11; wherein the tomography apparatus is formed as an X-ray computer tomography.

13. The reconstruction system according to claim 10, wherein the first data set is a data set recorded in a low-dose helical scan of said object under examination.

14. The reconstruction system according claim 10, wherein one of the first projection data set and the second projection data set is recorded by using a non-planar scanning path, and the other one of the projection data sets is recorded by using a planar scanning path.

15. The reconstruction system according to claim 10, wherein the second data set is a data set recorded in a circular cone-beam scan of said object under examination.

16. The reconstruction system according to claim 15, wherein the registration is one of the group comprising rigid registration and non-rigid registration.

17. The reconstruction system according to claim 10, wherein the first data set is a data set recorded in a low-dose helical scan of said object under examination.

18. The reconstruction system according to claim 10, wherein one of the first projection data set and the second projection data set is recorded by using a non-planar scanning path, and the other one of the projection data sets is recorded by using a planar scanning path.

19. The reconstruction system according to claim 10, further comprising performing a second pass correction on the fused image to remove artifacts from the fused image.

* * * * *